United States Patent

Mast et al.

[11] Patent Number: 5,989,077
[45] Date of Patent: Nov. 23, 1999

[54] CONNECTOR FOR IMPLANTABLE MEDICAL DEVICE

[75] Inventors: Roy T. Mast; Daniel J. Cooke, both of Lake Jackson, Tex.

[73] Assignee: Intermedics Inc, Angleton, Tex.

[21] Appl. No.: 09/039,025

[22] Filed: Mar. 13, 1998

[51] Int. Cl.[6] .................................................. H01R 4/36
[52] U.S. Cl. ........................................... 439/814; 439/804
[58] Field of Search .................................... 439/804, 805, 439/807, 808, 810, 811, 812, 813, 814, 815, 816, 817, 818, 819, 820, 821; 607/37

[56] References Cited

U.S. PATENT DOCUMENTS

| | | | |
|---|---|---|---|
| 3,238,496 | 3/1966 | Crowther | 439/811 |
| 3,304,392 | 2/1967 | Isler | 439/814 |
| 3,891,298 | 6/1975 | Yorgin et al. | 339/272 |
| 3,908,668 | 9/1975 | Boldue | 128/419 |
| 4,860,750 | 8/1989 | Frey et al. | |
| 5,005,104 | 4/1991 | Grunert et al. | 361/55 |

*Primary Examiner*—Lincoln Donovan
*Attorney, Agent, or Firm*—Schwegman, Lundberg, Woessner and Kluth

[57] ABSTRACT

A header assembly for coupling a cardiac lead to a cardiac stimulator is provided. The header assembly includes a header that has a bore for receiving one end of the cardiac lead. The bore has a first longitudinal axis. A connector housing is coupled to the header and has a second bore substantially aligned with the first bore. A biasing member is disposed within the connector housing and has a portion projecting into the second bore to bias the end of the cardiac lead against the walls of the second bore. A set-screw is threadedly coupled to the housing and is operable to secure the cardiac lead to the connector housing when tightened.

14 Claims, 8 Drawing Sheets

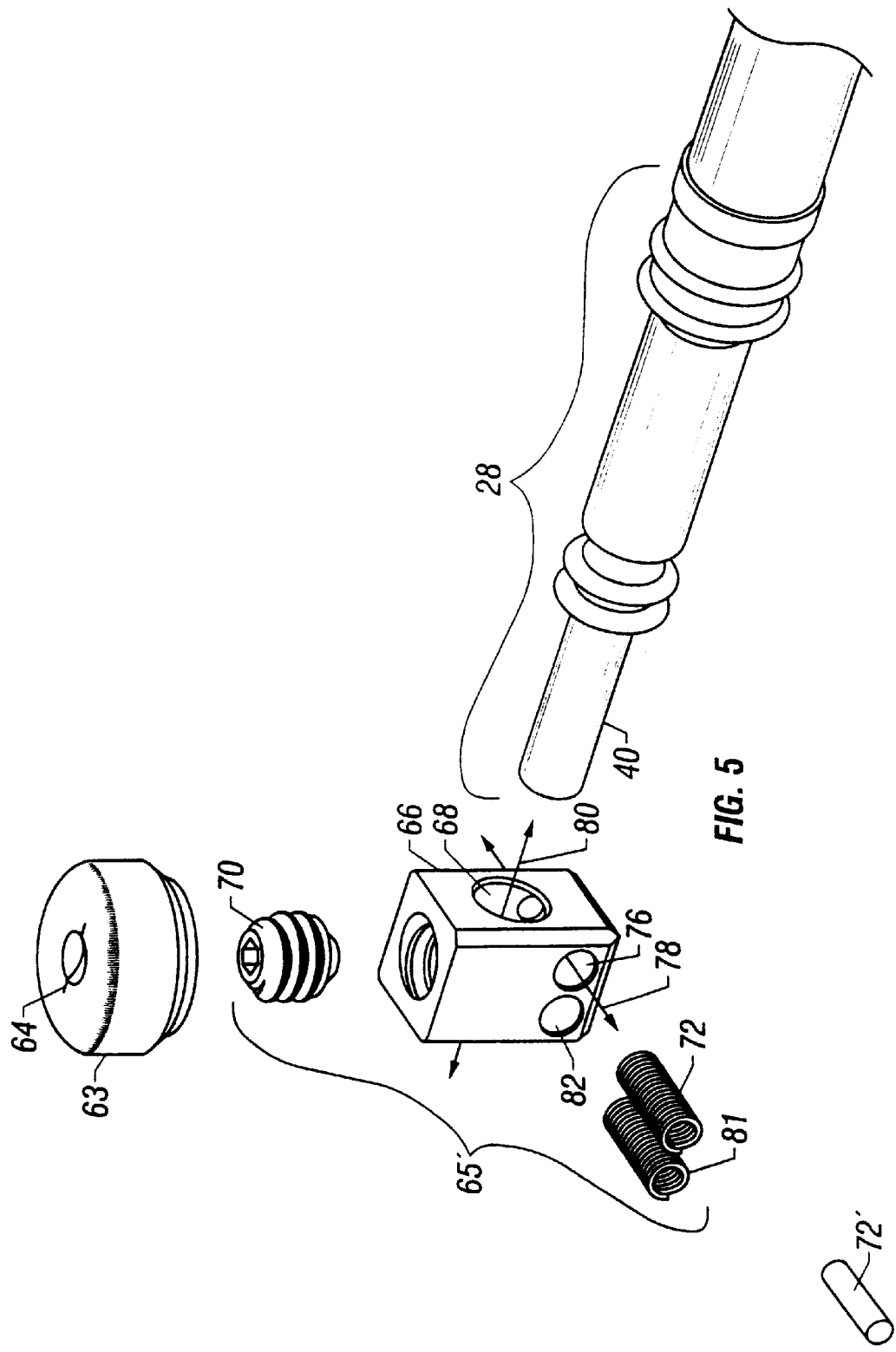

CONNECTOR FOR IMPLANTABLE MEDICAL DEVICE

BACKGROUND OF THE INVENTION

1. Field of the Invention

This invention relates generally to cardiac stimulation devices, and more particularly to apparatus for connecting a cardiac lead to a cardiac stimulator, such as a pacemaker or defibrillator.

2. Description of the Related Art

The course of treatment indicated for patients suffering from cardiac arrhythmia normally depends on a number of factors, such as the age of the patient, the type and severity of the arrhythmia, as well as other factors. Many patients may be successfully treated using drug therapy, surgical intervention, or a combination of the two. However, for some patients, the best course of treatment involves direct electrical stimulation of the affected area of the heart by means of an implanted cardiac stimulator.

Conventional implantable cardiac stimulator systems typically consist of a cardiac stimulator and one or more elongated leads. The cardiac stimulator may be a pacemaker, a defibrillator, a sensing instrument, or some combination thereof. The circuitry, batteries, and other components of the cardiac stimulator are ordinarily encased within a metallic housing commonly referred to as a "can." Most of the circuitry of the cardiac stimulator is mounted on a small electronic circuit board commonly known as a multi-chip module or hybrid microcircuit.

The proximal ends of the leads of the cardiac stimulator system are connected physically and electrically to the cardiac stimulator can via a structure commonly known as a header. The distal end of each lead is implanted near the site requiring electrical stimulation or sensing. The leads function to carry electrical stimulation signals from the cardiac stimulator can to the targeted tissue and to transmit sensing signals from the targeted tissue back to the cardiac stimulator can.

A typical header consists of a molded plastic or epoxy structure that encases one or more conductor wires emanating from the cardiac stimulator can. The header also includes one or more longitudinally disposed bores that are dimensioned to receive the proximal ends of the cardiac leads. One or more electrical contacts are provided inside the header and connected to the conductor wires of the header. The contacts are positioned near or around the bore to contact the metallic parts of the proximal ends of the leads. The proximal end of each lead is retained in the header by a set screw that is tightened by the physician at the time the cardiac stimulator system is implanted or by some other retention mechanism.

In a common procedure used by physicians to implant a new cardiac stimulator system, a lead is first implanted inside the body and manipulated so that the distal end of the lead is positioned proximate the targeted tissue. The proximal end of the lead is normally left protruding from the body during the implantation procedure so that it may be readily connected to the cardiac stimulator. After the distal end of the lead has been positioned inside the body, the proximal end of the lead is connected to the header by inserting it into a bore and tightening the set screw. Following connection of the lead, the cardiac stimulator is implanted under the patient's skin.

The electrical contacts inside the header are commonly tubular in shape or are provided with tubular passages and are fabricated with inner diameters that are larger than the outer diameters of the proximal ends of the leads to provide sliding fits between the contacts and the proximal ends of the leads. A sliding fit is preferable to enable the implanting physician to insert the proximal end of the lead with minimal effort and with little risk of damaging the lead or the header. As a result of the relatively loose fit between the contacts and the proximal ends of the leads, the leads may make only intermittent electrical contact or no contact at all with the header until the set screw is tightened. Reliable electrical conduction by the lead is not ensured until the set-screw is tightened. There will normally be some time lag between the moment when the proximal end of the lead is inserted into the header and when the set screw is tightened by the physician.

Most cardiac stimulator system patients will require replacement of all or part of their cardiac stimulator systems at some point in their lifetimes. Replacement may be indicated where the cardiac stimulator has exceeded its useful life span due to battery depletion or malfunction, or where the capabilities of the cardiac stimulator no longer match the arrhythmia condition of the patient. This may occur where the patient has undergone physiological changes as a result of disease, trauma, surgery or other causes. Replacement of a typical cardiac stimulator involves surgical excision of the stimulator, disconnection of the stimulator from the cardiac lead, and connection and implantation of a replacement cardiac stimulator.

Electrical stimulation of the heart will be interrupted from the time the old cardiac stimulator is disconnected from the lead until the new cardiac stimulator is fully connected to the lead and activated. As noted above, complete connection may not be reliably achieved until the set-screw is tightened. In most cases, the duration of the interruption will depend on the skill and speed of the surgeon, and on whether the surgeon must perform any diagnostic procedures on the lead or cardiac stimulator prior to tightening the set screw.

There are several disadvantages associated with conventional lead connection systems. As noted above, the mere insertion of the proximal end of the lead into the header does not guarantee immediate electrical stimulation of the heart. In situations where the lead does not make good contact upon insertion into the header, the patient may not receive electrical stimulation from the cardiac stimulator until the set screw is tightened. Some arrhythmia patients may be adversely impacted by even short interruptions in the application of electrical stimulus to the heart, even in circumstances where the surgeon has made efforts to minimize the disconnection time.

Another disadvantage stems from the way in which conventional leads are held in place in the header. The primary mechanism for retaining the lead in the header is the set screw. Many modern cardiac stimulators have an anticipated implant life span of five years or longer. Following implantation, the connection between the cardiac stimulator and the cardiac lead is subjected to a variety of stresses that stem from the patient's physical activity and/or the rhythmic motion of the patient's breathing and heart beat. Some patients even place stress on the connection by habitually palpating their implanted cardiac stimulators with their hands. High stresses may be imparted by physical trauma to the body. Years of exposure to such stresses may loosen the set screw. In the absence of some other engaging mechanism, the lead may disconnect from the header.

The present invention is directed to overcoming, or reducing the effect of one or more of the foregoing disadvantages.

SUMMARY OF THE INVENTION

In accordance with one aspect of the present invention, a header assembly for coupling cardiac lead to a cardiac stimulator is provided. The header assembly includes a header that has a first bore that has a first longitudinal axis for receiving one end of the electrical lead. A connector housing is coupled to the header and has a second bore substantially aligned with the first bore. A biasing member is disposed within the connector housing. The biasing member has a portion projecting into the second bore to bias the end of the cardiac lead against the walls of the second bore. A set-screw is threadedly coupled to the housing and is operable to secure the cardiac lead to the connector housing when tightened.

In accordance with another aspect of the present invention, a header assembly for coupling cardiac lead to a cardiac stimulator is provided. The header assembly includes a header that has a bore that has a first longitudinal axis for receiving one end of the cardiac lead. A connector housing is coupled to the header and has a second bore substantially aligned with the first bore. The header assembly is provided with means for biasing the end of the cardiac lead against the walls of the second bore. A set-screw is threadedly coupled to the housing and is operable to secure the cardiac lead to the connector housing when tightened.

In accordance with still another aspect of the present invention, a connector assembly for connecting a cardiac lead to a header of a cardiac stimulator is provided. The connector assembly includes a connector housing that has a first bore for receiving one end of the cardiac lead, a second bore disposed transverse to the first bore, and a third bore terminating in the first bore. A biasing member is disposed in the second bore and has a portion projecting into the first bore to bias the end of the cardiac lead. A set-screw is disposed in the third bore.

In accordance with still another aspect of the present invention, a header assembly for coupling a cardiac lead to a cardiac stimulator is provided. The header assembly includes a header that has a first bore that has a first longitudinal axis for receiving one end of the cardiac lead, and a second bore disposed transverse to the first bore. A biasing member is disposed in the second bore and has a portion projecting into the first bore to bias the end of the cardiac lead against the walls of the first bore. A set-screw is threadedly coupled to the header and is operable to secure the cardiac lead to the header when tightened.

BRIEF DESCRIPTION OF THE DRAWINGS

The foregoing and other advantages of the invention will become apparent upon reading the following detailed description and upon reference to the drawings in which:

FIG. 5 is a pictorial view like FIG. 3 of an alternate embodiment of the connector assembly in accordance with the present invention;

FIG. 6 is a pictorial view of an alternate embodiment of the biasing member depicted in FIG. 3;

DETAILED DESCRIPTION OF SPECIFIC EMBODIMENTS

Figure 1:
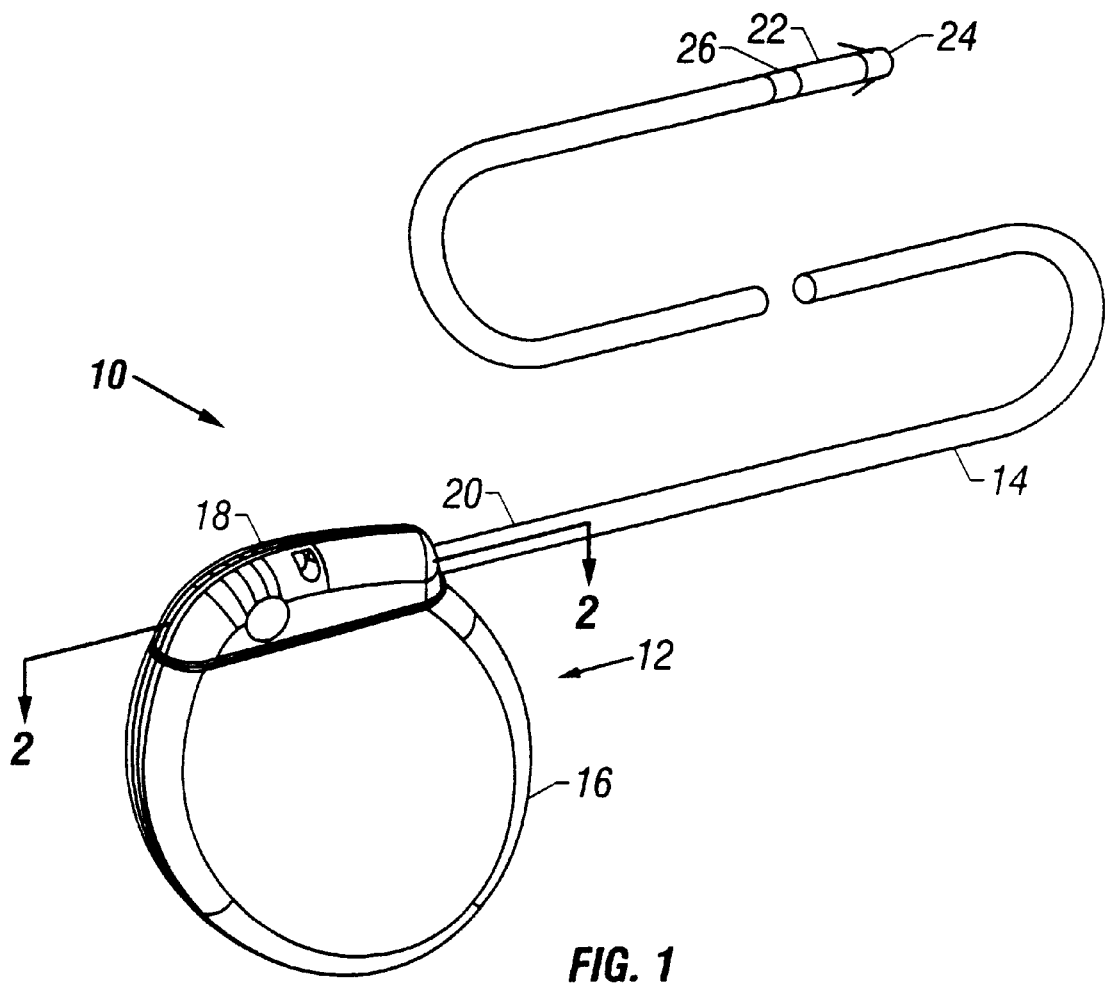
FIG. 1 is a pictorial view of an exemplary embodiment of a cardiac stimulator system in accordance with the present invention.

In the drawings described below, reference numerals are generally repeated where identical elements appear in more than one figure. Turning now to the drawings, and in particular to FIG. 1, there is shown an exemplary implantable cardiac stimulator system 10 that may be suitable for either endocardial or epicardial stimulation of a human heart (not shown). The cardiac stimulator system 10 includes a cardiac stimulator 12 and a cardiac lead 14. The lead 14 is of such length that it is shown broken. The cardiac stimulator 12 consists of a can 16 composed of titanium, or like materials, connected to a header assembly 18. The can 16 encases the electronic components of the cardiac stimulator 12, which may include storage cells, power transistors, microprocessors, telemetry circuits, sensors, and induction coils for rechargeable storage cells, among others. It should be understood that the term "cardiac stimulator" may refer to a pacemaker, a defibrillator, a sensing instrument, or some combination of these devices.

The proximal end 20 of the lead 14 is connected to the header assembly 18. The distal end 22 of the lead 14 terminates in a tip electrode 24 that is designed to be attached to the tissue requiring electrical stimulation. The lead 14 is depicted in a bipolar configuration. Accordingly, the lead 14 is provided with a second electrode 26 that is located proximal to the tip electrode 24. However, the skilled artisan will appreciate that unipolar arrangements are also possible.

Figure 2:
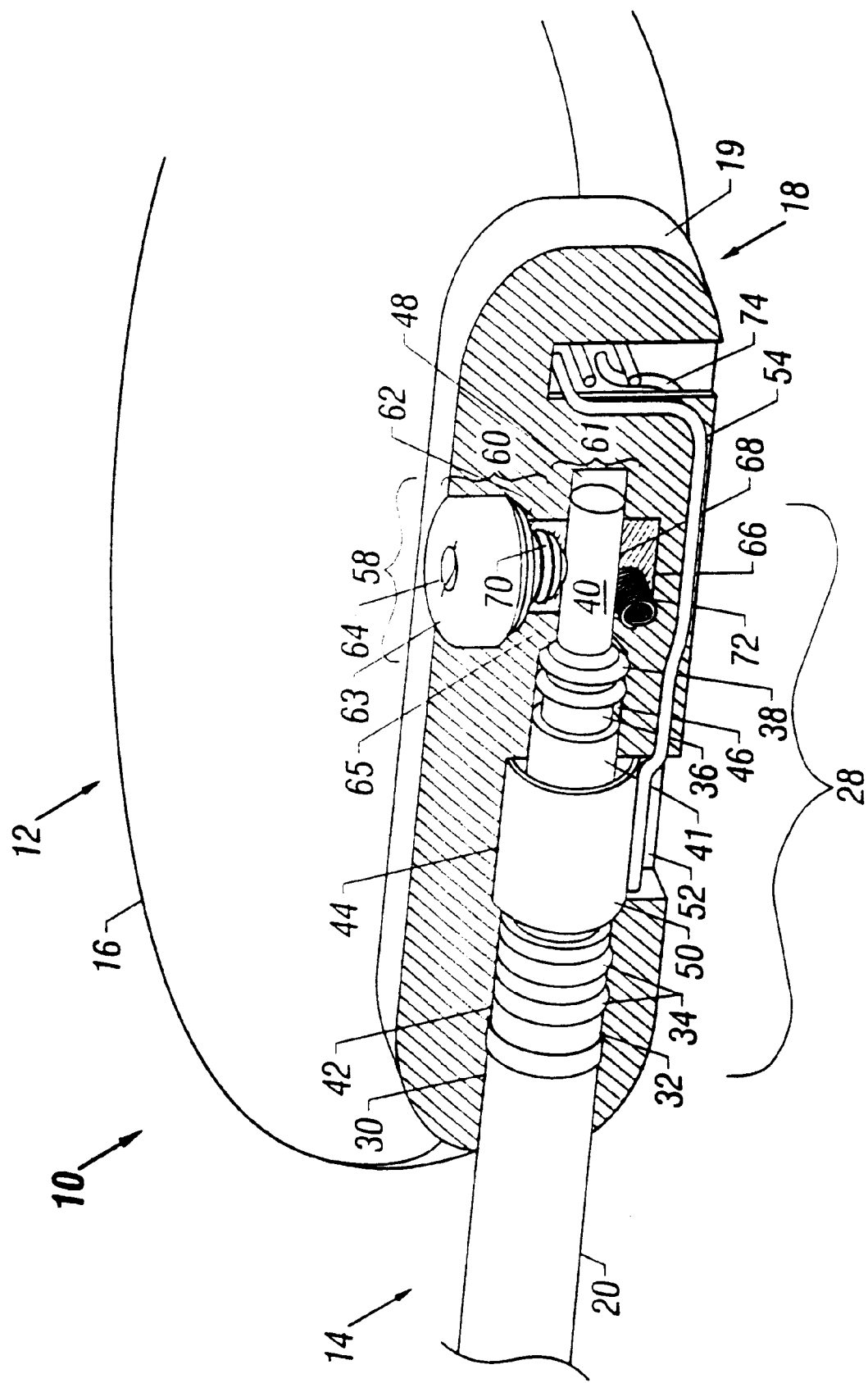
FIG. 2 is a cross-sectional view of FIG. 1 taken at section 2—2.

The detailed structure of the header assembly 18 and the connection thereof with the lead 14 may be understood by referring now also to FIG. 2, which is a cross-sectional view of FIG. 1 taken at section 2—2. The header assembly 18 includes a header 19 composed of epoxy, molded plastic or like materials. The proximal end 20 of the lead 14 includes a connector 28 that is disposed within a longitudinal bore 30 in the header 19. The connector 28 has three segments, a distal segment 32 that is provided with O-rings 34, an intermediate segment 36 that is provided with O-rings 38, and a proximal segment 40. The intermediate segment 36 includes a tubular contact 41 that is in electrical communication with the electrode 26 via a conductor wire inside the lead 14 (not shown). The proximal segment 40 is in electrical communication with the tip electrode 24 via a conductor wire (not shown) running inside the lead 14.

The bore 30 includes four sections, a distal section 42, an intermediate section 44, an intermediate section 46, and a proximal section 48. The distal section 42 is sized to accommodate the distal segment 32 and to provide sealing engagement with the O-rings 34 to restrict the influx of body fluids that might impede electrical performance. The proximal section 48 of the bore 30 is sized to axially receive the proximal segment 40 of the connector assembly 28. The intermediate section 46 is sized to accommodate the intermediate segment 36 and to provide sealing engagement with the O-rings 38, again to restrict the influx of body fluids that might impede electrical performance. The intermediate section 44 is provided with a tubular metallic contact 50 that is designed to make electrical contact with the contact 41. The tubular contact 50 is placed in the intermediate section 44 via an opening 52 that leads from the exterior of the header 19 to the intermediate section 44. The opening 52 is sealed with epoxy, silicone rubber or like adhesives after insertion of the contact 50. An electrical pathway between the tubular contact 50 and the circuitry inside the can 16 is established by a conductor wire 54 that is connected at one end to the contact 50. The other end of the conductor wire 54 is fed into the interior of the can 16.

The header 19 is provided with a bore 58 that is countersunk and is divided into a cylindrical upper portion 60 and a rectangular lower portion 61 delineated by an annular shoulder 62. The upper portion 60 is capped by a septum 63 which is coupled to the header 19 and seated at a lower end on the annular shoulder 62. The septum 63 is secured to the header 19 by a suitable biocompatible medical grade adhesive, such as silicone adhesive or like adhesives. The septum 63 is provided with a slot 64, the function of which is discussed below.

A connector assembly 65 is disposed in the bore 58. The connector assembly 65 includes a rectangular housing 66 that is seated in the lower portion 61 of the bore 58. The housing 66 has a longitudinal bore 68 that is aligned with the proximal section 48 of the bore 30 so that the proximal segment 40 of the connector 28 is axially received in the housing 66. A set-screw 70 is threadedly connected to the housing 66 to retain the proximal end 40 within the housing 66. The slot 64 in the septum 63 is provided to permit a wrench (not shown) to be inserted through the septum 63 to tighten or loosen the set-screw 70 as necessary. A biasing member 72 is disposed in the housing 66 and functions to bias the proximal segment 40 into contact with the walls of the bore 68 and to retain the proximal segment 40 within the housing 66. The housing 66 functions as an electrical contact to carry signals to and from the proximal segment 40. An electrical pathway between the housing 66 and the can 16 is established by a conductor wire 74 that is fed at one end into the can 16 and is connected at the other end to the housing 66 (not visible in FIG. 2).

The housing 66 and set screw 70 are advantageously fabricated from a biocompatible metallic material, such as stainless steel, MP35N alloy, titanium or similar materials. The septum 63 is preferably composed of biocompatible molded plastic, silicone rubber or like materials.

Figure 3:
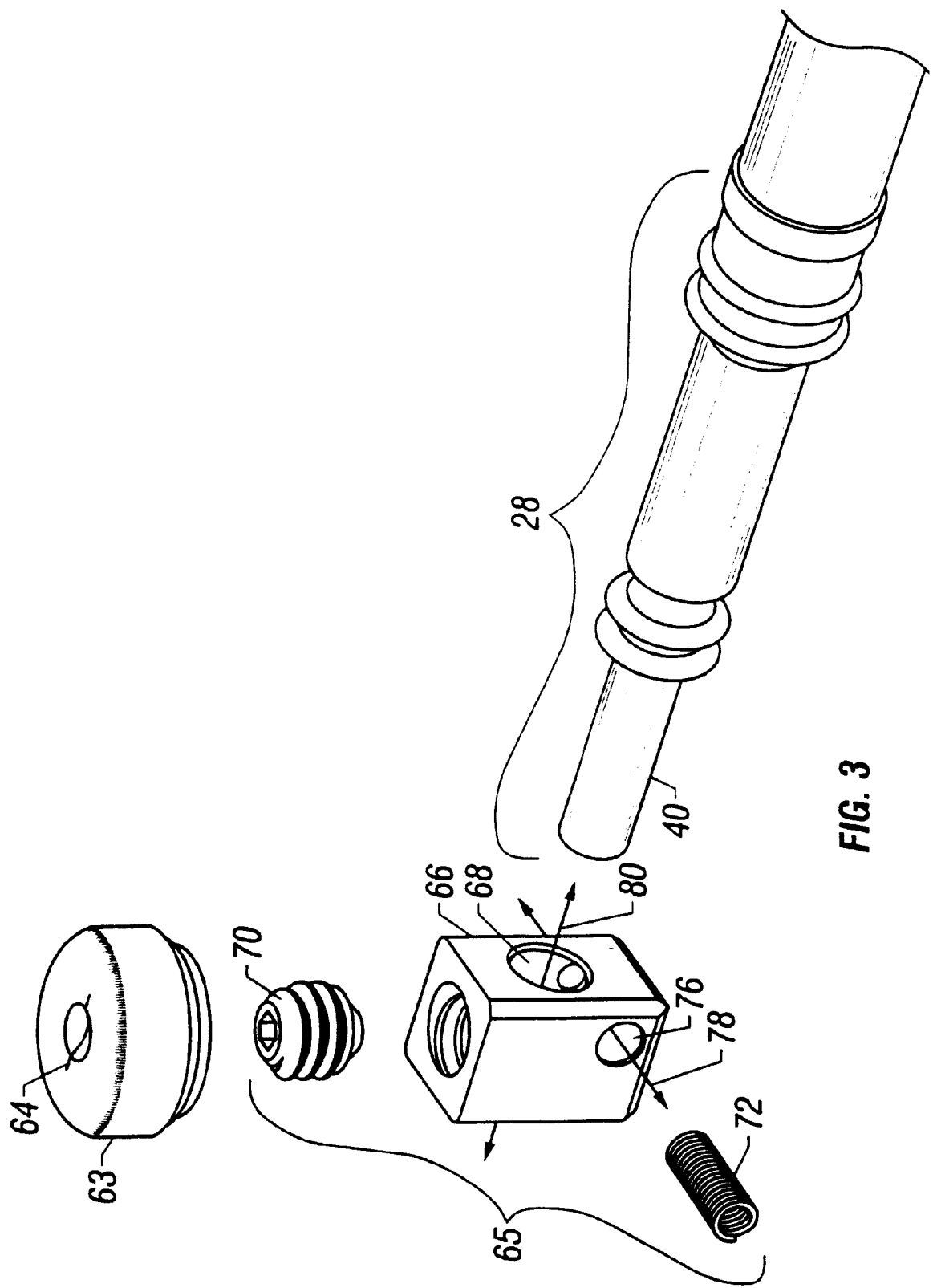
FIG. 3 is an exploded pictorial view of an exemplary embodiment of a connector assembly in accordance with the present invention.
Figure 4:
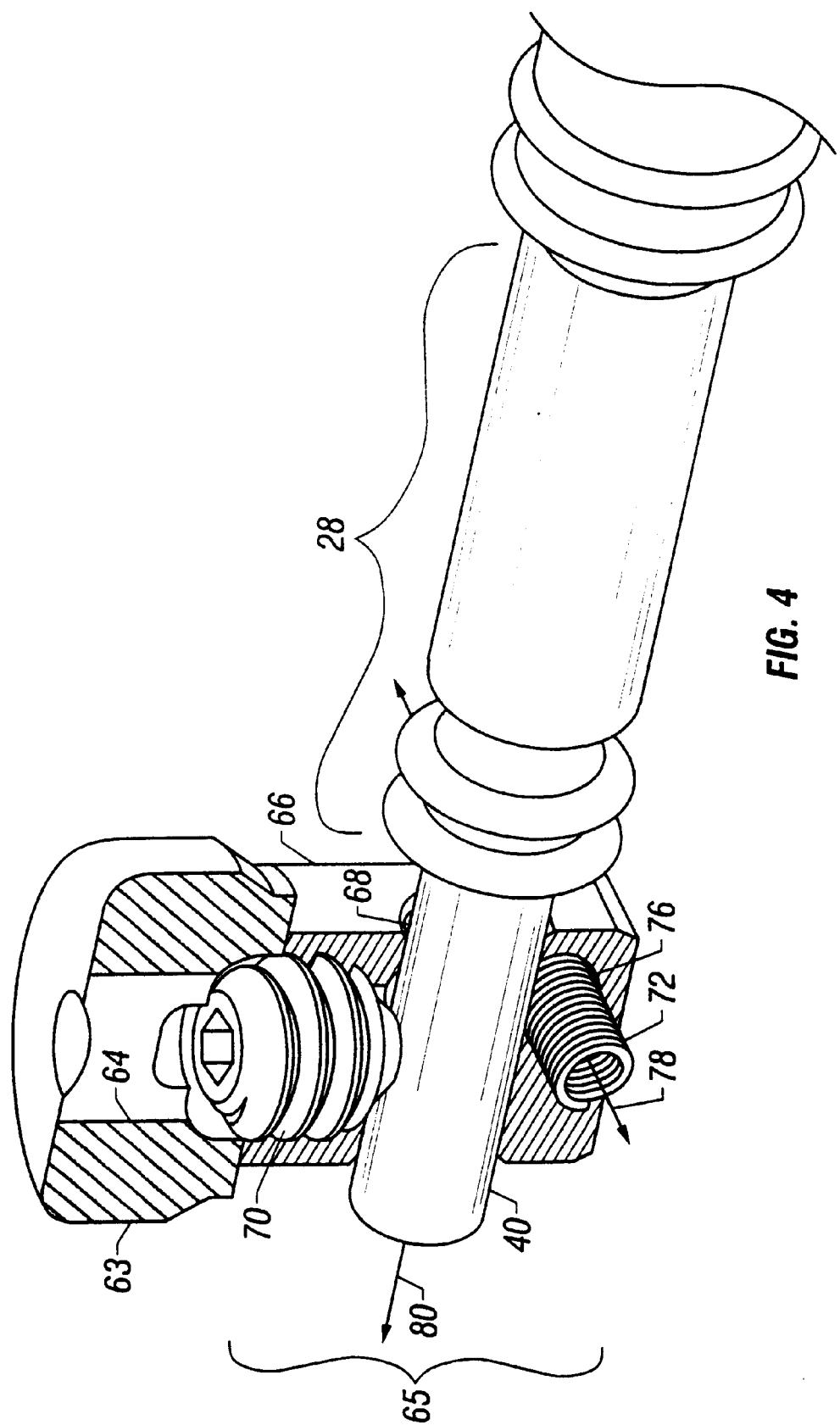
FIG. 4 is an unexploded partial sectional view of FIG. 3 in accordance with the present invention.

The detailed structure of the connector assembly 65 may be understood by referring now also to FIGS. 3 and 4. FIG. 3 is an exploded pictorial view of the connector assembly 65 and the lead connector 28. FIG. 4 is a pictorial view of the connector assembly 65 with the housing 66 and the septum 63 shown in section. As noted above, the bore 68 is oriented to be aligned with the proximal section 48 of the bore 30 (see FIG. 2) when the housing 66 is seated in the lower section 62 of the bore 58. The biasing member 72 is disposed in a bore 76 in the housing 66 that runs transverse to the bore 68. The bore 76 is offset vertically from the bore 68 so that when the biasing member 72 is disposed in the bore 76, the set-screw 70 may be fully tightened down without interfering with the biasing member 72. Note that the bore 76 and the bore 68 are relatively disposed so that a portion of the biasing member 72 projects into the bore 68. In this way, the biasing member 72 engages the proximal segment 40 of the connector 28 when the proximal segment 40 is inserted into the bore 68. As shown in FIG. 3, the longitudinal axis 78 of the bore 76 may be normal to the longitudinal axis 80 of the bore 68, but need not be so long as the relative orientations of the bores 76 and 68 permit a portion of the biasing member 72 to project into the bore 68.

The biasing member 72 biases the proximal segment 40 against the upper wall of the bore 68. Force is applied to the proximal segment 40 in essentially one direction to ensure that the proximal segment 40 is in continuous contact with the walls of the bore 68 immediately upon insertion into the bore 68 and before the set-screw 70 is tightened. As a result, electrical signals may be passed from the cardiac stimulator 12 to the heart as soon as the proximal segment 40 is inserted into the bore 68. In addition, the biasing member 72 will resist disconnection of the proximal segment 40 from the housing 66 in the event the set-screw 70 loosens after implantation.

FIG. 5 is a pictorial view like FIG. 3 and depicts an alternate embodiment of the connector assembly, now designated 65. FIG. 5 illustrates that the connector assembly 65 may be fitted with a second biasing member 81 disposed in a bore 82 in the housing 66 that is configured like the bore 76. Additional biasing members may be provided as their number and spacing is a matter of design discretion.

The biasing member 72 may be fabricated in a variety of configurations to provide the desired spring effect. In the embodiments depicted in FIGS. 2, 3, 4, and 5, the biasing members 72 are 81 are coiled springs composed of stainless steel or like biocompatible metallic materials. In an alternative embodiment shown in FIG. 6, the biasing member, now designated 72' may be formed from an elastomer, such as polyurethane or like materials.

Figure 7:
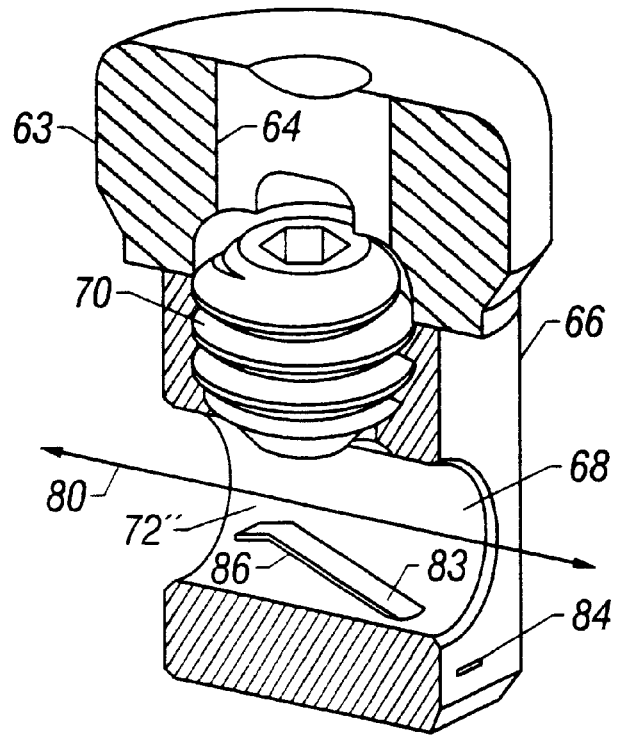
FIG. 7 is a sectional view like FIG. 4 of an alternate embodiment of the connector assembly in accordance with the present invention.

FIG. 7 is a view similar to FIG. 4 and depicts another alternate embodiment of the biasing member, now designated 72". The biasing member 72" may consist of an elongated leaf spring that projects upward into the bore 68 at an angle with respect to the longitudinal axis 80 of the bore 68. One end 83 of the leaf spring 72" passes through the lower portion of the housing 66 and is welded to the exterior of the housing at 84. The other end 86 projects into the bore 68. The leaf spring 72" may be stainless steel or like materials. There may be multiple springs 72".

Figure 8:
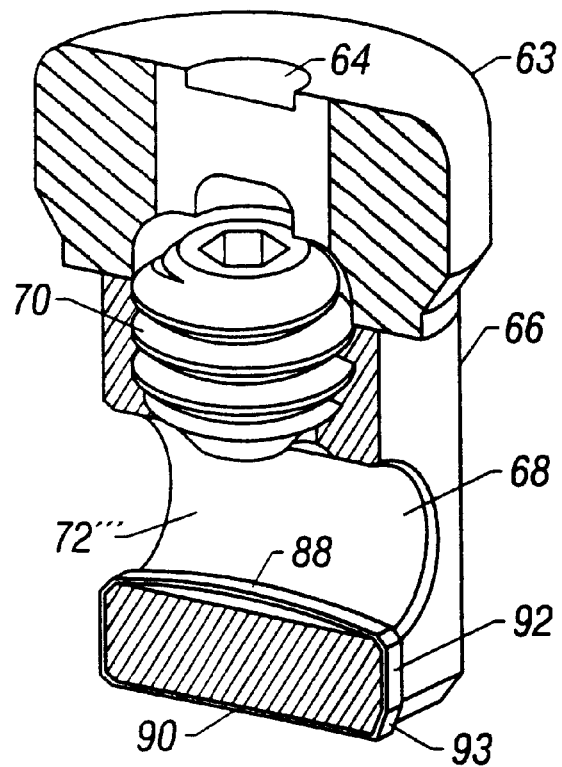
FIG. 8 is a cross-sectional view like FIG. 7 of another alternate embodiment of the connector assembly in accordance with the present invention.
Figure 9:
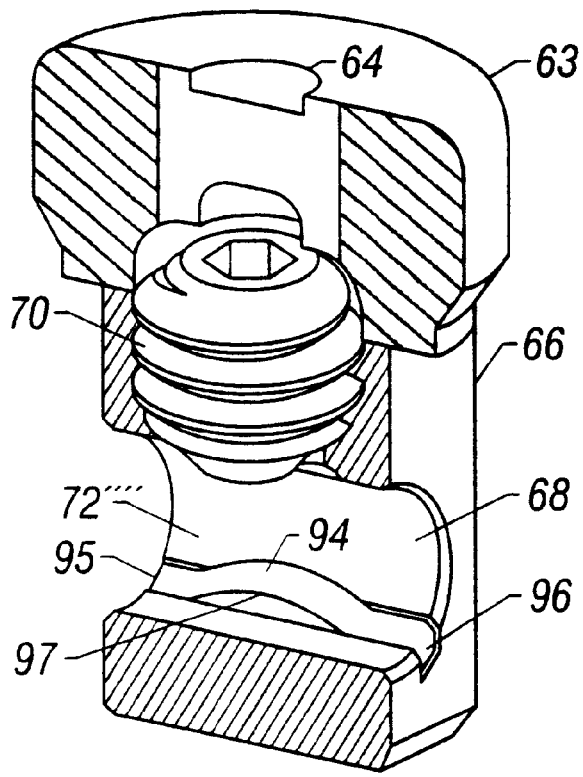
FIG. 9 is a cross-sectional view like FIG. 7 of another alternate embodiment of the connector assembly in accordance with the present invention.

As shown in FIGS. 8 and 9, a myriad of alternative arrangements are possible for the biasing member. FIG. 8 is a sectional view like FIG. 7, and depicts an alternative biasing member, now designated 72'''. The biasing member 72''' consists of a clip member with an arcuate portion 88 that projects into the bore 68 and a lower portion 90 that engages the bottom of the housing 66. The biasing member 72''' snaps into position and is retained by friction. A slot 92 is machined in the housing 66 to enable the biasing member 72''' to be seated so that the end 93 of the biasing member 72''' is relatively flush with the side of the housing 66. FIG. 9 is a sectional view like FIG. 8 of another alternative arrangement of the biasing member, now designated 72''''. The biasing member 72'''' has an arcuate member 94 projecting into the bore 68. Each end 95 and 96 of the biasing member 72'''' is disposed in a longitudinal slot 97 formed in the bore 68. The end 96 is secured to the housing 66 by welding.

Figure 10:
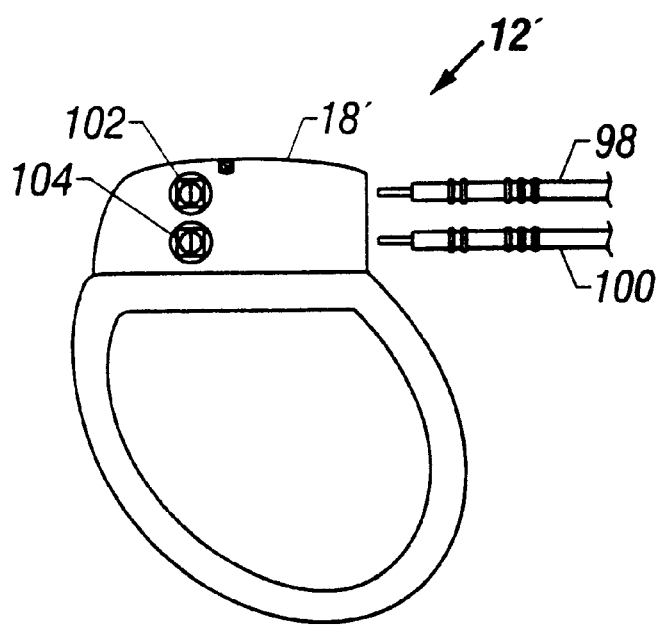
FIG. 10 is a front view of an alternate embodiment of a cardiac stimulator in accordance with the present invention.

FIG. 10 depicts a front view of an alternate embodiment of the cardiac stimulator, now designated 12, which is capable of connecting to two cardiac leads 98 and 100 for dual-chamber or other dual-site cardiac stimulation. The header assembly, now designated 18', is provided with two connector assemblies 102 and 104, each like the connector assembly 65 shown in FIG. 3. Additional connector assemblies may be provided to accommodate multiple lead cardiac stimulators. The particular arrangement of the connector assemblies 102 and 104 and any additional assemblies is a matter of design discretion.

Figure 11:
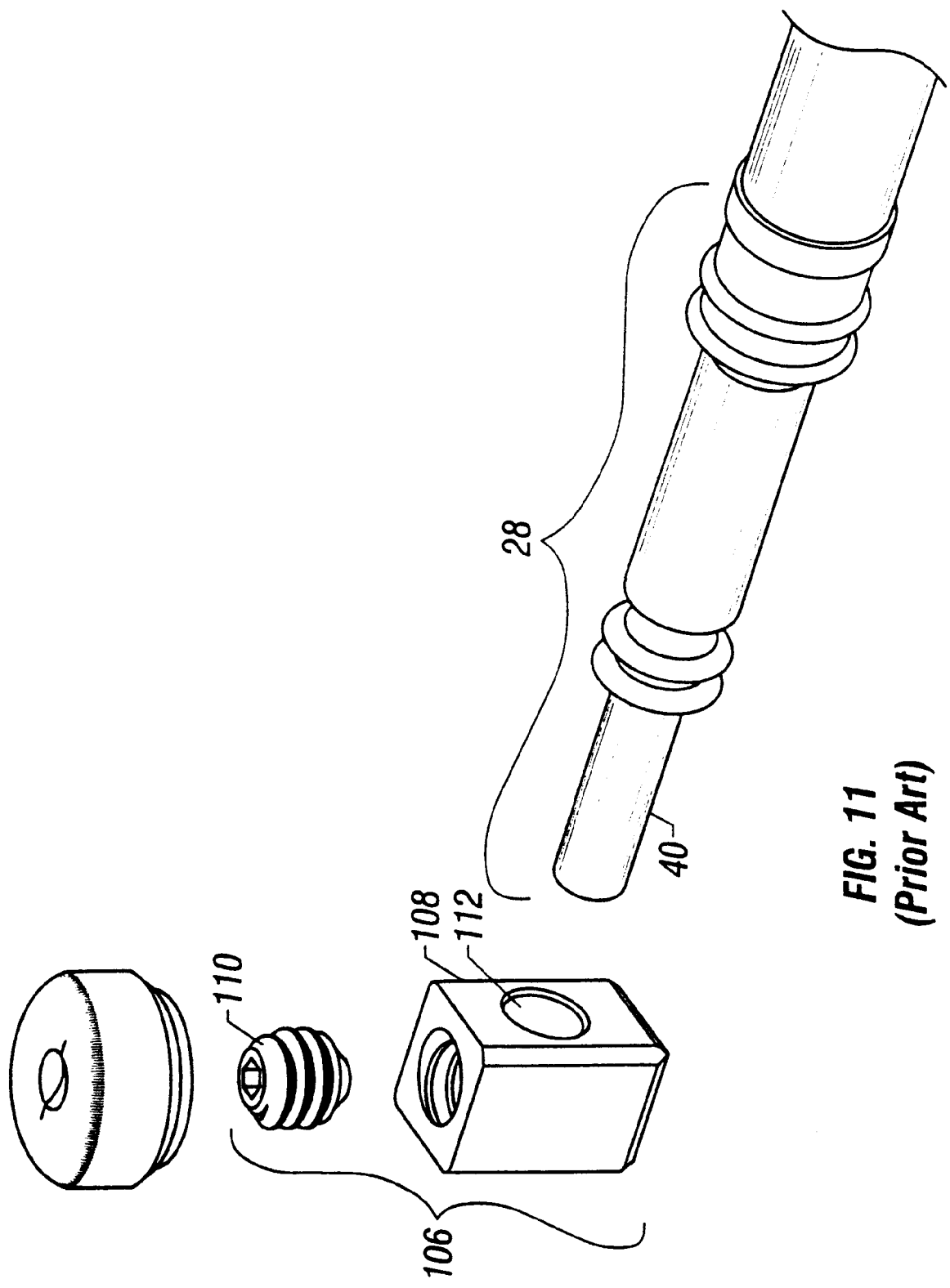
FIG. 11 is an exploded pictorial view of a conventional connector assembly for a cardiac stimulator.

The contrast between the present invention and a conventional connector assembly may be understood by referring to FIGS. 2 and 11. FIG. 11 is an exploded pictorial view of a conventional connector assembly 106. The conventional connector assembly 106 includes a housing 108 and a set-screw 110, but does not include the biasing members of the aforementioned embodiments. The housing 108 includes a bore 112 for receiving the proximal segment 40 of the connector 28. As noted above, the relatively loose fit between the inner diameter of the bore 112 and the outer diameter of the proximal segment 40 may result in undesirably intermittent electrical contact between the proximal segment 40 and the housing 108. Furthermore, the proximal segment 40 may disconnect from the housing 108 if the set-screw loosens, since there is no additional mechanism to retain the proximal segment 40 in the housing 108.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A header assembly for coupling a cardiac lead to a cardiac stimulator, comprising:

a header having a bore for receiving one end of the cardiac lead, the bore having a first longitudinal axis;

a connector housing coupled to the header and having a second bore aligned with the first bore;

a biasing member disposed within the connector housing, the biasing member having a portion projecting into the second bore to bias the end of the cardiac lead against the walls of the second bore; and a set screw independent from said biasing member, said set screw threadedly coupled to the housing and being operable to secure the cardiac lead to the connector housing when tightened.

2. The header assembly of claim 1, wherein the biasing member comprises a coiled spring having a second longitudinal axis transverse to the first longitudinal axis.

3. The header assembly of claim 2, wherein the biasing member is disposed so that the second longitudinal axis is substantially normal to the first longitudinal axis.

4. The header assembly of claim 1, wherein the biasing member comprises a leaf spring.

5. A header assembly for coupling cardiac lead to a cardiac stimulator comprising:

a header having a bore for receiving one end of the cardiac lead, the bore having a first longitudinal axis;

a connector housing coupled to the header and having a second bore aligned with the first bore;

means for biasing the end of the cardiac lead against the walls of the second bore; and a set screw not connected to said means for biasing, said set screw threadedly coupled to the housing and being operable to secure the cardiac lead to the connector housing when tightened.

6. The header assembly of claim 5, wherein the means for biasing the end of the cardiac lead comprises a coiled spring having a second longitudinal axis transverse to and offset from the first longitudinal axis.

7. The header assembly of claim 5, wherein the means for biasing the end of the cardiac lead comprises an elastomeric spring.

8. The header assembly of claim 5, wherein the means for biasing the end of the cardiac lead comprises a leaf spring.

9. A connector assembly for connecting a cardiac lead to a header of a cardiac stimulator, comprising:

a connector housing having a first bore for receiving one end of the cardiac lead, a second bore disposed transverse to and offset from the first bore, and a third bore terminating in the first bore;

a biasing member disposed in the second bore and having a portion projecting into the first bore to bias the end of the cardiac lead; and a set screw disposed in the third bore and adapted to be advanced into said first bore.

10. The connector assembly of claim 9, wherein the biasing member comprises a coiled spring.

11. The connector assembly of claim 9, wherein the biasing member comprises an elastomeric spring.

12. A header assembly for coupling cardiac lead to a cardiac stimulator, comprising:

a header having a first bore having a first longitudinal axis for receiving one end of the cardiac lead and a cross section perpendicular to said first longitudinal axis, and a second bore having a second longitudinal axis and a cross section perpendicular to said second longitudinal axis, said second longitudinal axis being disposed transverse to the first bore, said second bore intersecting said first bore with less than all of said cross sections of said first and second bores;

a biasing member disposed in the second bore and having a portion projecting into the first bore to bias the end of the cardiac lead against the walls of the first bore; and a set screw threadedly coupled to the header and being operable to secure the cardiac lead to the header when tightened.

13. The header assembly of claim 12, wherein the biasing member comprises a coiled spring.

14. The header assembly of claim 12, wherein the biasing member comprises an elastomeric spring.

* * * * *